(12) United States Patent
Prior

(10) Patent No.: US 10,667,800 B2
(45) Date of Patent: Jun. 2, 2020

(54) FOUR BAR ARTICULATION MECHANISM FOR TISSUE SPECIMEN RETRIEVAL DEVICE

(71) Applicant: COVIDIEN LP, Mansfield, MA (US)

(72) Inventor: Scott J. Prior, Shelton, CT (US)

(73) Assignee: Covidien LP, Mansifled, MA (US)

(*) Notice: Subject to any disclaimer, the term of this patent is extended or adjusted under 35 U.S.C. 154(b) by 219 days.

(21) Appl. No.: 15/974,071

(22) Filed: May 8, 2018

(65) Prior Publication Data
US 2019/0343499 A1 Nov. 14, 2019

(51) Int. Cl.
*A61B 17/00* (2006.01)

(52) U.S. Cl.
CPC ........... *A61B 17/00234* (2013.01); *A61B 2017/00287* (2013.01); *A61B 2017/00367* (2013.01); *A61B 2017/00424* (2013.01)

(58) Field of Classification Search
CPC ............ A61B 17/00234; A61B 17/221; A61B 17/32056; A61B 17/26; A61B 2017/00287; A61B 2017/00367; A61B 2017/2212; A61B 2017/2215; A61B 2017/2217
See application file for complete search history.

(56) References Cited

U.S. PATENT DOCUMENTS

| | | | |
|---|---|---|---|
| 5,354,303 A * | 10/1994 | Spaeth | A61B 17/00234 604/171 |
| 5,643,283 A | 7/1997 | Younker | |
| 6,059,793 A | 5/2000 | Pagedas | |
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |

(Continued)

FOREIGN PATENT DOCUMENTS

| WO | 2004002334 A1 | 1/2004 |
|---|---|---|
| WO | 2014158880 A1 | 10/2014 |

*Primary Examiner* — Ashley L Fishback
(74) *Attorney, Agent, or Firm* — Carter, DeLuca & Farrell, LLP

(57) ABSTRACT

A tissue specimen retrieval device includes a housing having an outer shaft that extends distally therefrom and that defines a longitudinal axis. An end effector assembly is included that extends distally from the outer shaft in a deployed position of the end effector assembly. A first actuator is operably associated with the housing and actuatable to deploy and retract the end effector assembly. A second actuator is operably associated with the housing and actuatable to move a four-bar articulation mechanism including first, second and third movable links and a stationary link coupled together by respective first, second and third pivots. Actuation of the second actuator moves the first link distally which forces the second and third links to rotate in opposing directions about the first and second pivots which, in turn, forces at least one of the first or second links against the end effector assembly to articulate the same.

17 Claims, 5 Drawing Sheets

(56) References Cited

U.S. PATENT DOCUMENTS

| | | |
|---|---|---|
| 6,344,026 B1 | 2/2002 | Burbank et al. |
| 6,350,266 B1 | 2/2002 | White et al. |
| 6,350,267 B1 | 2/2002 | Stefanchik |
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,645,283 B2 | 1/2010 | Reynolds et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,452 B2 | 10/2016 | Menn et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,629,618 B2 | 4/2017 | Davis et al. |
| 9,642,638 B1 | 5/2017 | Carrier |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |

\* cited by examiner

FOUR BAR ARTICULATION MECHANISM FOR TISSUE SPECIMEN RETRIEVAL DEVICE

BACKGROUND

Technical Field

The present disclosure relates to tissue specimen retrieval from an internal body cavity and, more particularly, to articulation mechanisms for tissue specimen retrieval devices and tissue specimen retrieval devices incorporating the same to facilitate retrieval of a tissue specimen from the internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment.

SUMMARY

The present disclosure provides articulation mechanisms for tissue specimen retrieval devices to facilitate retrieval of the tissue specimen from the internal body cavity. These and other aspects and features of the present disclosure are detailed below. As used herein, the term "distal" refers to the portion that is described which is further from a user, while the term "proximal" refers to the portion that is being described which is closer to a user. Further, any or all of the aspects and features described herein, to the extent consistent, may be used in conjunction with any or all of the other aspects and features described herein.

Provided in accordance with aspects of the present disclosure is a tissue specimen retrieval device including a housing having an outer shaft extending distally therefrom and defining a longitudinal axis therethrough. An end effector assembly extends distally from the outer shaft in a deployed position of the end effector assembly. A first actuator is operably associated with the housing and is actuatable to deploy and retract the end effector assembly. A second actuator is operably associated with the housing and actuatable to selectively move a four-bar articulation mechanism. The four-bar articulation mechanism includes first, second and third movable links and a stationary link coupled together by respective first, second and third pivots. Actuation of the second actuator moves the first link distally which forces the second and third links to rotate in opposing directions about the first and second pivots while the third link is anchored by the third pivot which, in turn, forces at least one of the first or second links against the end effector assembly to articulate the same.

In aspects according to the present disclosure, the second link is forced to rotate in a counterclockwise direction and the third link is forced to rotate in a clockwise direction. In other aspects, the second link includes an abutting surface which, when rotated, forces an arm of the end effector assembly to articulate.

In yet other aspects according to the present disclosure, the end effector assembly includes first and second arms configured to support a tissue specimen bag thereon. In other aspects, deployment of the end effector assembly automatically unfurls the tissue specimen bag. The end effector assembly may be deployable relative to the outer shaft from a retracted position, wherein the end effector assembly is disposed within the outer shaft, to a deployed position.

In still other aspects, the first actuator is actuated in one direction from an un-actuated position to an actuated position and in an opposite direction from the actuated position back to the un-actuated position. Yet in other aspects, actuation of the first actuator in a proximal direction corresponds to deployment of the end effector assembly a distal direction. Actuation of the second actuator in a first direction may correspond to actuation of the first link in a second direction.

In accordance with other aspects of the present disclosure a tissue specimen retrieval device includes a housing having an outer shaft that extends distally therefrom and that defines a longitudinal axis. An end effector assembly is selectively deployable and retractable from the outer shaft by a first actuator. A four-bar articulation mechanism is selectively actuatable and includes first, second and third movable links and a stationary link coupled together by respective first, second and third pivots. The four-bar articulation mechanism is actuatable to force the first link distally which forces the second and third links to rotate in opposing directions about the first and second pivots while the third link is anchored by the third pivot which, in turn, forces at least one of the first or second links against the end effector to articulate the same.

In aspects according to the present disclosure, the second link is forced to rotate in a counterclockwise direction and the third link is forced to rotate in a clockwise direction. In other aspects, the end effector assembly includes first and second arms configured to support a tissue specimen bag thereon. In still other aspects, the second link includes an abutting surface which, when rotated, forces at least one of the first and second arms of the end effector assembly to articulate. In yet other aspects, deployment of the end effector assembly automatically unfurls the tissue specimen bag.

In aspects according to the present disclosure the end effector assembly is deployable relative to the outer shaft from a retracted position, wherein the end effector assembly is disposed within the outer shaft, to a deployed position. In yet other aspects, actuation of the first actuator in a proximal direction corresponds to deployment of the end effector assembly in a distal direction. Still in other aspects, the four-bar articulation mechanism is selectively actuatable by a second actuator and wherein actuation of the second actuator in a first direction corresponds to actuation of the first link in a second direction.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
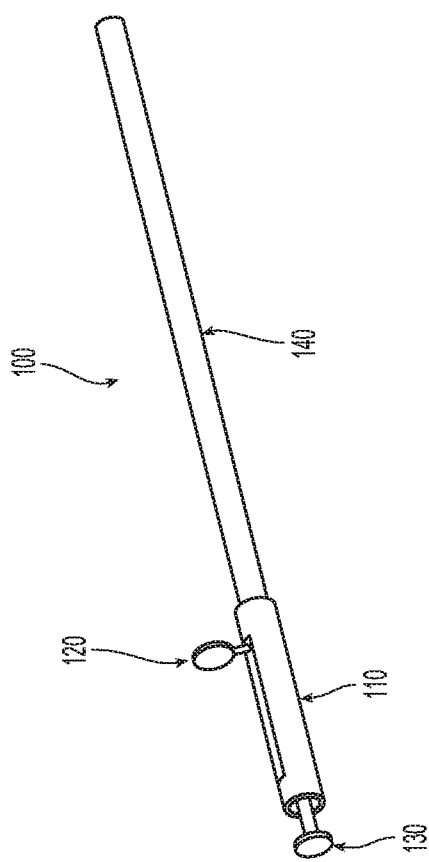
FIG. 1 is a side, perspective view of a tissue specimen retrieval device provided in accordance with aspects of the present disclosure, wherein an end effector assembly of the tissue specimen retrieval device is disposed in a retracted position.

The present disclosure provides articulation mechanisms for tissue specimen retrieval devices to facilitate retrieval of tissue from the internal body cavity.

Turning to FIGS. 1-4B, a tissue specimen retrieval device provided in accordance with the present disclosure is shown generally identified by reference numeral 100. Tissue specimen retrieval device 100 includes a housing 110, first and second actuators 120, 130 operably associated with housing 110, an outer shaft 140 extending distally from housing 110, an end effector assembly 150 selectively deployable from the distal end of outer shaft 140, and four-bar articulation mechanism 180 configured to enable selective articulation of end effector assembly 150 relative to outer shaft 140 in the deployed position of end effector assembly 150.

Housing 110, although illustrated as defining a generally tubular configuration, may define any suitable configuration to facilitate grasping and manipulating tissue specimen retrieval device 100 such as, for example, a pencil-grip configuration, a pistol-grip configuration, etc., and may include any suitable features to enhance ergonomics such as, for example, recesses, protrusions, textured surfaces, finger rings, etc.

First actuator 120 is operably associated with housing 110 and coupled to outer shaft 140 to enable selective extension and retraction of outer shaft 140 relative to housing 110 and, thus, end effector assembly 150, to selectively move end effector assembly 150 between a retracted position (FIG. 1) and a deployed position (FIG. 2) relative to outer shaft 140 in response to actuation of first actuator 120. Alternatively, first actuator 120 may be coupled to end effector assembly 150 to enable selective extension and retraction of end effector assembly 150 relative to housing 110 and, thus, outer shaft 140, to similarly move end effector assembly 150 between a retracted position (FIG. 1) and a deployed position (FIG. 2) relative to outer shaft 140. First actuator 120 may be configured as a sliding actuator slidable along housing 110, as illustrated, or may define any other suitable configuration such as, for example, a plunger actuator that is selectively manipulatable relative to housing 110 along a longitudinal axis of housing 110, a pivoting actuator pivotable relative to housing 110, etc.

Second actuator 130 is operably associated with housing 110 and coupled to articulation mechanism 180 (FIGS. 4A-4B) to enable selective articulation of end effector assembly 150 relative to outer shaft 140, once deployed from outer shaft 140, between an aligned position (FIG. 2) and an articulated position (FIG. 3), in response to actuation of second actuator 130. Second actuator 130 may be configured as a plunger actuator that is selectively manipulatable relative to housing 110 along a longitudinal axis of housing 110, as illustrated, or may define any other suitable configuration such as, for example, a pivoting actuator pivotable relative to housing 110, a sliding actuator slidable along housing 110, etc.

Figure 2:
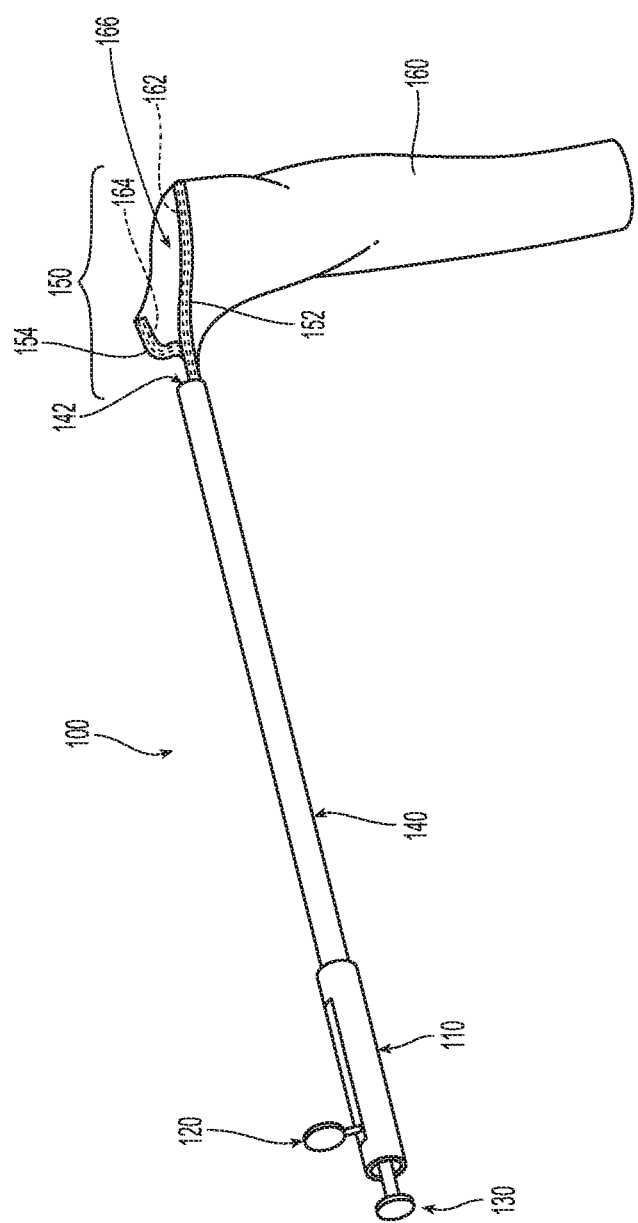
FIG. 2 is a side, perspective view of the tissue specimen retrieval device of FIG. 1, wherein the end effector assembly is disposed in a deployed, aligned position.
Figure 3:
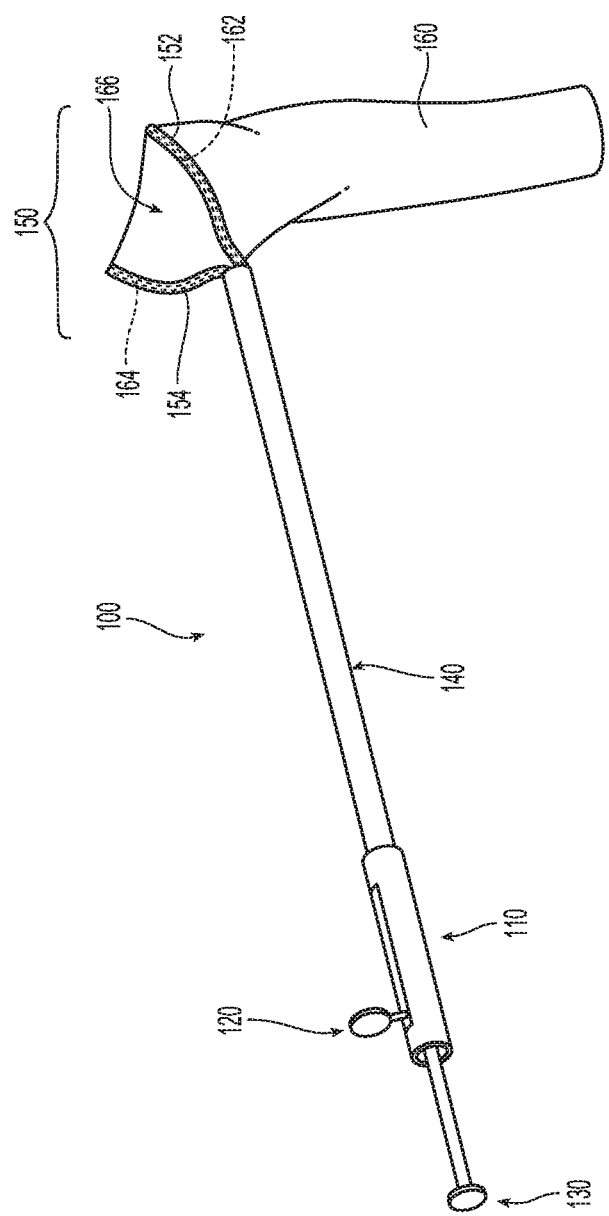
FIG. 3 is a side, perspective view of the tissue specimen retrieval device of FIG. 1, wherein the end effector assembly is disposed in a deployed, articulated position.
Figure 5:
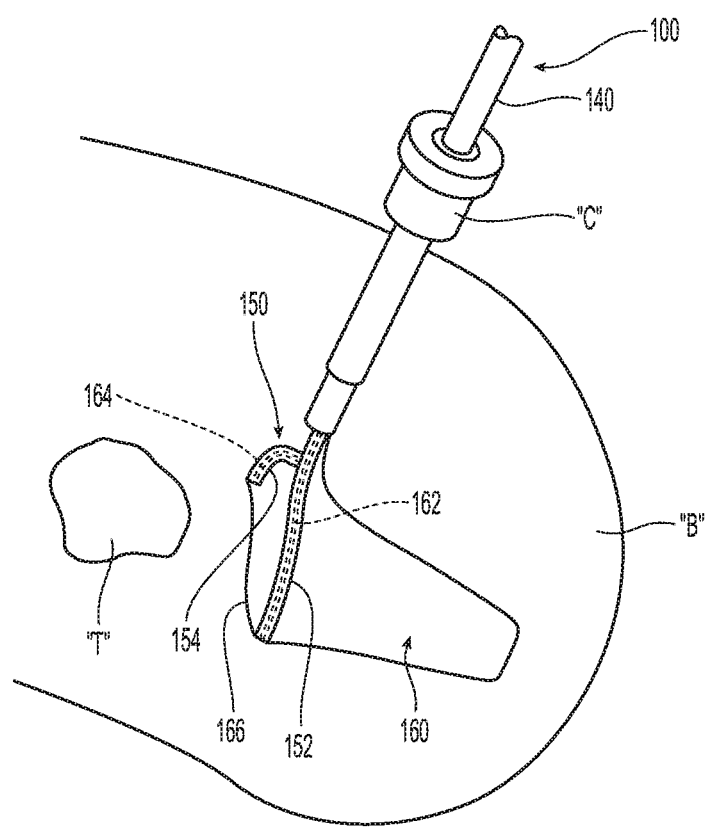
FIG. 5 is a perspective view of the tissue specimen retrieval device of FIG. 1 inserted through an access cannula into an internal body cavity for retrieval of a tissue specimen therefrom.

Continuing with reference to FIGS. 1-3, outer shaft 140 extends distally from housing 110, as noted above, and is configured for insertion through an access cannula "C" (FIG. 5) or natural passageway into an internal body cavity "B" (FIG. 5). Outer shaft 140 may be substantially rigid (within manufacturing tolerances and in response to reasonable loads applied thereto) or may include one or more portions configured to flex and/or articulate relative to a longitudinal axis thereof. A lumen 142 extends longitudinally through outer shaft 140. Outer shaft 140, as noted above, is slidable relative to housing 110 and end effector assembly 150 to enable selective deployment of end effector assembly 150 from outer shaft 140. More specifically, outer shaft 140 is movable between a distal position, corresponding to the retracted position of end effector assembly 150 (see FIG. 1), wherein end effector assembly 150 is disposed within lumen 142 defined in outer shaft 140, and a proximal position, corresponding to the deployed position of end effector assembly 150 (FIG. 2), wherein end effector assembly 150 extends distally from outer shaft 140. As an alternative to outer shaft 140 moving relative to housing 110 to deploy end effector assembly 150, as also noted above, end effector assembly 150 may be selectively movable relative to housing 110 and outer shaft 140 to enable deployment of end effector assembly 150 from outer shaft 140 from the retracted position (FIG. 1) to the deployed position (FIG. 2).

End effector assembly 150 includes a pair of arms 152, 154 and a tissue specimen bag 160 depending from arms 152, 154. Arms 152, 154 are configured for positioning within one or more channels 162, 164 formed about at least a portion of open end 166 of tissue specimen bag 160 to retain tissue specimen bag 160 on arms 152, 154. In the retracted position of end effector assembly 150, arms 152, 154 may be resiliently flexed inwardly to enable accommodation of arms 152, 154 within lumen 142 of outer shaft 140. Tissue specimen bag 160 may be furled, folded, or otherwise positioned in the retracted position of end effector assembly 150 to enable accommodation of tissue specimen bag 160 within lumen 142 of outer shaft 140. Upon deployment of end effector assembly 150 from outer shaft 140, arms 152, 154 are configured to resiliently return to a spaced-apart, curved configuration for retaining tissue specimen bag 160 thereon in an open condition, thus enabling insertion of a tissue specimen "T" (FIG. 5) through open end 166 of tissue specimen bag 160 and into the interior thereof. The resilient return of arms 152, 154 may also serve to unfold, unfurl, or otherwise manipulate tissue specimen bag 160 upon deployment from outer shaft 140.

Tissue specimen bag 160 may be formed from any suitable bio-compatible material (or materials), e.g., ripstop nylon, configured to retain a tissue specimen "T" (FIG. 5) therein. As noted above, tissue specimen bag 160 depends from arms 152, 154 in the deployed position of end effector assembly 150 such that articulation of arms 152, 154 likewise articulates tissue specimen bag 160. Tissue specimen bag 160 defines at least one opening, e.g., at open end 166 thereof, and includes one or more channels 162, 164 formed about open end 166 thereof for receipt of arms 152, 154, respectively, therein. The one or more channels 162, 164 may be separate or in communication with one another, and/or may extend about only a portion of open end 166 of tissue specimen bag 160 or about the entirety perimeter thereof. One or more of the openings of tissue specimen bag 160, e.g., open end 166, may include a cinch cord (not shown) disposed thereabout to enable selective closure of the opening. Tissue specimen bag 160 may be disengaged from arms 152, 154 upon cinching closed open end 166 of tissue specimen bag 160, retraction of end effector assembly 150 back towards the retracted position (FIG. 1), using a separate instrument, e.g., grasping device, and/or in any other suitable manner.

With additional reference to FIGS. 4A and 4B, four-bar articulation mechanism 180 is shown. Articulation mechanism 180 includes movable links 181a, 181b and 181c which cooperate with a stationary link 181d to articulate the tissue specimen bag 160 from an aligned configuration (FIG. 4A showing a partially exposed configuration) to an articulated configuration (FIG. 4B). Movable link 181a connects to movable link 181b about pivot 182a, movable link 181b connects to movable link 181c about pivot 182b, and movable link 181c connects to stationary link 181d about pivot 182c. When disposed in the aligned configuration of FIG. 2, links 181a, 181b and 181c are configured in a parallel, chain-like orientation from a proximal portion to a distal portion of the outer shaft 140 and stationary link 181d runs parallel on an adjacent side of outer shaft 140 (See FIG. 4A).

Upon selective actuation of actuator 120 in a proximal direction, arms 152, 154 are exposed in a generally aligned orientation with outer shaft 140 and tissue specimen bag 160 unfurls therefrom (See FIG. 2). Actuator 130 may then be selectably actuated to articulate arms 152, 154 and tissue specimen bag 160. More particularly, actuation of actuator 130 urges link 181a distally which forces link 181b to rotate in a counterclockwise direction and link 181c to rotate in a clockwise direction about pivots 182a, 182b, respectively, while pivot 182c is anchored to link 181d. When forced in this fashion, an abutting surface 185 of link 181b urges arm 152 (and/or 154) to articulate as needed. In embodiments, the third link 181c may be configured to also assist in articulation of the end effector 150. The direction of actuation of actuators 120 and 130 may be reversed depending upon a particular purpose or to achieve a particular result.

In embodiments, a rotation knob (not shown) associated with housing 110 and operably coupled to end effector assembly 150 may be provided to enable selective rotation of end effector assembly 150 about the longitudinal axis of outer shaft 140 and relative to housing 110.

Figure 4:
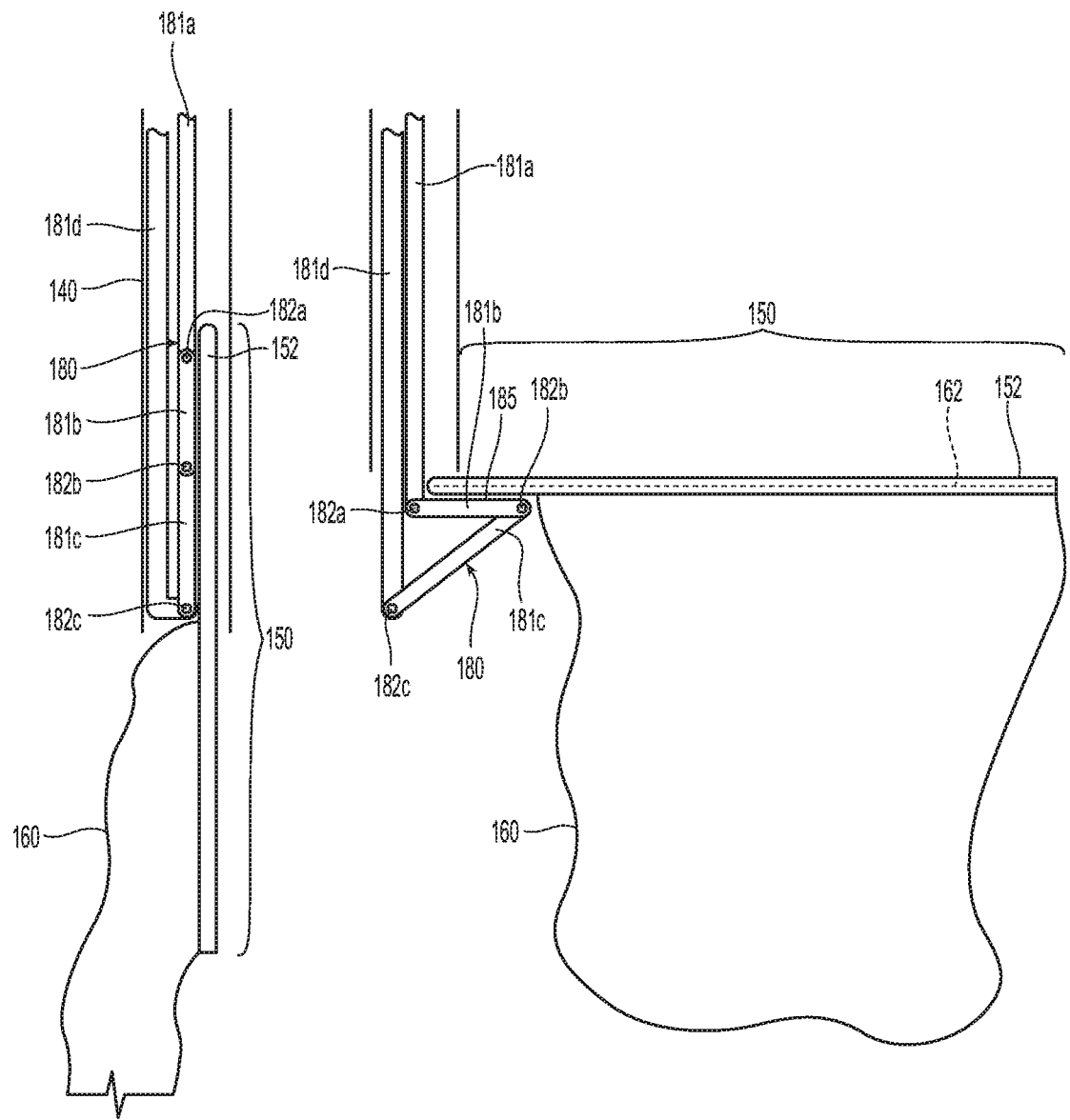
FIG. 4A is a side, partial cross-sectional view of the tissue specimen retrieval device of FIG. 1 and the end effector assembly disposed in a partially extended and aligned positon.
FIG. 4B is a side, partial cross-sectional view of the tissue specimen retrieval device of FIG. 1 and the end effector assembly disposed in the deployed, articulated position.

With reference to FIGS. 1-4B and 5, and initially to FIGS. 1 and 4A, in use, end effector assembly 150 is initially disposed in the retracted position to facilitate insertion of tissue specimen retrieval device 100 through an access cannula "C" (FIG. 5) or natural passageway into an internal body cavity "B" (FIG. 5). Link 181a is initially disposed in a proximal-most position to maintain end effector assembly 150 and tissue specimen bag 160 within outer shaft 140.

Once tissue specimen retrieval device 100 is disposed within the internal body cavity "B" (FIG. 5) as desired, and with reference to FIGS. 2 and 4A, 4B, end effector assembly 150 is deployed from outer shaft 140 by actuating first actuator 120 from a more-distal position to a more-proximal position to thereby withdraw outer shaft 140 proximally from about end effector assembly 150 such that end effector assembly 150 is deployed to the deployed positon. At this point, end effector assembly 150 remains aligned on the longitudinal axis of outer shaft 140.

Referring to FIG. 4B, if it is desired to articulate end effector assembly 150 relative to outer shaft 140 after end effector assembly 150 is deployed from outer shaft 140, second actuator 130 is moved proximally from a closer position relative to housing 110 to a further proximally-spaced position relative to housing 110 to thereby slide link 181a distally to deploy the four-bar articulation mechanism 180 and articulate end effector assembly 150. Although both actuator 120 and actuator 130 are shown as having an inverse or opposite actuation effect when actuated (e.g., proximal actuation yields distal advancement of link 181a), there may be a direct correlation between actuation of either actuator 120 or 130 and the actual actuation effect (e.g., distal actuation yields distal advancement of link 181a).

In embodiments, the arms 152, 154 may be spring biased such that, once deployed from the distal end of the outer shaft 140, the arms 152, 154 open to facilitate unfurling of the tissue specimen bag 160. In other embodiments, a lock (not shown) may be included with either or both actuating mechanisms 120, 130 to enable a user to lock the end effector assembly 150 in a deployed position for manipulation or lock the end effector assembly 150 in a particular articulated position. If a rotation mechanism is contemplated as mentioned above, a lock (not shown) may be utilized for this purpose as well. Any type of known locking mechanism is contemplated for this purpose.

Turning momentarily to FIG. 5, the above-detailed articulation of end effector assembly 150 of tissue specimen retrieval device 100 facilitates orientation of open end 166 of tissue specimen bag 160 in an appropriate position within the internal body cavity "B" to facilitate positioning of a tissue specimen "T" therein. End effector assembly 150 may be returned to the retracted position, which also serves to return end effector assembly 150 to the aligned position, by actuating second actuator 130 to move the four-bar articulating mechanism 180 (moving link 181a proximally) to generally align end effector assembly 150 with outer shaft 140. First actuator 120 is then actuated from the more-proximal position to the more-distal position to advance outer shaft 140 about end effector assembly 150. As such, end effector assembly 150 is moved to the aligned position and returned to the retracted position to facilitate retrieval of end effector assembly 150 from the internal body cavity "B."

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
   a housing;
   an outer shaft extending distally from the housing and defining a longitudinal axis;
   an end effector assembly extending distally from the outer shaft in a deployed position of the end effector assembly;
   a first actuator operably associated with the housing and actuatable to deploy and retract the end effector assembly; and
   a second actuator operably associated with the housing and actuatable to selectively move a four-bar articulation mechanism, the four-bar articulation mechanism including first, second and third movable links and a stationary link coupled together by respective first, second and third pivots, wherein actuation of the second actuator moves the first link distally which forces the second and third links to rotate in opposing directions about the first and second pivots while the third link is anchored by the third pivot which, in turn, forces at least one of the first or second links against the end effector assembly to articulate the same.

2. The tissue specimen retrieval device according to claim 1, wherein the second link is forced to rotate in a counterclockwise direction and the third link is forced to rotate in a clockwise direction.

3. The tissue specimen retrieval device according to claim 1, wherein the second link includes an abutting surface which, when rotated, forces an arm of the end effector assembly to articulate.

4. The tissue specimen retrieval device according to claim 1, wherein the end effector assembly includes first and second arms configured to support a tissue specimen bag thereon.

5. The tissue specimen retrieval device according to claim 4, wherein deployment of the end effector assembly automatically unfurls the tissue specimen bag.

6. The tissue specimen retrieval device according to claim 1, wherein the end effector assembly is deployable relative to the outer shaft from a retracted position, wherein the end effector assembly is disposed within the outer shaft, to a deployed position.

7. The tissue specimen retrieval device according to claim 1, wherein the first actuator is actuated in one direction from an un-actuated position to an actuated position and in an opposite direction from the actuated position back to the un-actuated position.

8. The tissue specimen retrieval device according to claim 1, wherein actuation of the first actuator in a proximal direction corresponds to deployment of the end effector assembly a distal direction.

9. The tissue specimen retrieval device according to claim 1, wherein actuation of the second actuator in a first direction corresponds to actuation of the first link in a second direction.

10. The tissue specimen retrieval device according to claim 1, wherein actuation of the first actuator in a proximal direction corresponds to deployment of the end effector assembly in a distal direction.

11. The tissue specimen retrieval device according to claim 1, wherein the four-bar articulation mechanism is selectively actuatable by a second actuator and wherein actuation of the second actuator in a first direction corresponds to actuation of the first link in a second direction.

12. A tissue specimen retrieval device, comprising:
    a housing;
    an outer shaft extending distally from the housing and defining a longitudinal axis;
    an end effector assembly selectively deployable and retractable from the outer shaft by a first actuator; and
    a four-bar articulation mechanism including first, second and third movable links and a stationary link coupled together by respective first, second and third pivots, the four-bar articulation mechanism selectively actuatable to force the first link distally which forces the second and third links to rotate in opposing directions about the first and second pivots while the third link is anchored by the third pivot which, in turn, forces at least one of the first or second links against the end effector assembly to articulate the same.

13. The tissue specimen retrieval device according to claim 12, wherein the second link is forced to rotate in a counterclockwise direction and the third link is forced to rotate in a clockwise direction.

14. The tissue specimen retrieval device according to claim 12, wherein the end effector assembly includes first and second arms configured to support a tissue specimen bag thereon.

15. The tissue specimen retrieval device according to claim 14, wherein the second link includes an abutting surface which, when rotated, forces at least one of the first and second arms of the end effector assembly to articulate.

16. The tissue specimen retrieval device according to claim 14, wherein deployment of the end effector assembly automatically unfurls the tissue specimen bag.

17. The tissue specimen retrieval device according to claim 12, wherein the end effector assembly is deployable relative to the outer shaft from a retracted position, wherein the end effector assembly is disposed within the outer shaft, to a deployed position.

* * * * *